United States Patent
Hayman (10) Patent No.: US 9,040,945 B1
(45) Date of Patent: May 26, 2015

(54) METHOD OF MECHANICALLY CONTROLLING THE AMOUNT OF ENERGY TO REACH A PATIENT UNDERGOING INTRAOPERATIVE ELECTRON RADIATION THERAPY

(71) Applicant: Precision Accelerators of Louisiana LLC, New Orleans, LA (US)

(72) Inventor: Jonathan S. Hayman, New Orleans, LA (US)

( * ) Notice: Subject to any disclaimer, the term of this patent is extended or adjusted under 35 U.S.C. 154(b) by 0 days.

(21) Appl. No.: 14/206,938

(22) Filed: Mar. 12, 2014

Related U.S. Application Data (60) Provisional application No. 61/777,286, filed on Mar. 12, 2013.

(51) Int. Cl.
*A61N 5/00* (2006.01)
*A61N 5/10* (2006.01)
*G21K 5/04* (2006.01)

(52) U.S. Cl.
CPC ............ *A61N 5/1075* (2013.01); *A61N 5/1078* (2013.01); *A61N 2005/1096* (2013.01); *A61N 2005/1089* (2013.01)

(58) Field of Classification Search
CPC ....... A61B 18/18; A61M 1/3681; A61N 5/10; A61N 5/1042; A61N 5/1077; G21K 5/04
USPC .......... 250/505.1, 492.1, 492.3, 491.1; 600/1, 600/2; 378/65
See application file for complete search history.

(56) References Cited

U.S. PATENT DOCUMENTS

| | | | |
|---|---|---|---|
| 5,037,374 A | 8/1991 | Carol | |
| 6,381,304 B1 * | 4/2002 | Shoenfeld et al. | 378/65 |
| 7,834,336 B2 | 11/2010 | Boeh et al. | |
| 8,073,105 B2 | 12/2011 | Gertner et al. | |
| 8,094,779 B2 | 1/2012 | Gertner | |
| 8,106,371 B2 | 1/2012 | Fujii et al. | |
| 8,269,197 B2 * | 9/2012 | Goer et al. | 250/492.3 |
| 2014/0275708 A1 * | 9/2014 | Leek | 600/1 |

OTHER PUBLICATIONS

.decimal, Inc. .decimal® Products—Bolus Electron Conformal Therapy (ECT) http://www.dotdecimal.com/products/ect.

* cited by examiner

*Primary Examiner* — Nikita Wells
(74) *Attorney, Agent, or Firm* — Garvey, Smith, Nehrbass & North, L.L.C.; Seth M. Nehrbass; Mackenzie D. Rodriguez (57) ABSTRACT

Apparatus for performing electron radiation therapy on a breast cancer patient preferably includes an intraoperative electron radiation therapy machine, an intraoperative electron radiation therapy collimator tube connected to the intraoperative electron radiation therapy machine, and a plurality of filters made of a material having substantially the same density as human breast tissue for placement between the machine and the patient to change the energy of a monoenergetic beam after the beam has left the machine, allowing a filter to be chosen to reduce the energy traveling through the tube to a desired amount of energy to treat the patient. A method of controlling the amount of energy to reach a breast cancer patient undergoing electron radiation therapy includes selecting a filter made of a material having substantially the same density as human tissue and placing the filter between an intraoperative electron radiation therapy machine and a breast cancer patient to change the energy of a monoenergetic beam after it has left the machine, the filter being chosen to reduce the energy traveling from the machine to a desired amount of energy to treat the patient.

28 Claims, 7 Drawing Sheets

METHOD OF MECHANICALLY CONTROLLING THE AMOUNT OF ENERGY TO REACH A PATIENT UNDERGOING INTRAOPERATIVE ELECTRON RADIATION THERAPY

CROSS-REFERENCE TO RELATED APPLICATIONS

Priority of U.S. Provisional Patent Application, Ser. No. 61/777,286, filed on Mar. 12, 2013 and incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to Radiation Therapy. More particularly, the present invention relates to Intraoperative Radiation Therapy.

2. General Background of the Invention

Intraoperative Radiation Therapy (IORT) is the use of radiation to treat cancers during surgery. Two types of treatment exist: X-ray and Electron Beam. While there are numerous effective uses of both treatments, there are few that are considered either economically competitive or medically superior to alternative treatments. With the use of electron beam linear accelerators, teams around the world have proven that Intraoperative Electron Radiation Therapy (IOERT) is equivalent to External Beam Radiation Therapy or Intensity Modulated Radiation Therapy for early breast cancer. Moreover, it is believed to be six times more cost efficient, reducing the cost of treating certain cancers from $30,000 to $5,000 (anticipated Medicare reimbursement rate in 2014).

There are two reasons IOERT technology has not been adopted in the United States. First, the US Government does not reimburse the treatment through Medicare, preventing market participants from profiting from ownership. Second, the inability to share machines between hospitals limits the number of market participants to those that have the critical mass of breast cancer cases to provide IOERT services profitably.

Even when Medicare does begin reimbursement for IOERT, the number of cases required to provide IOERT services profitably, limits the market to extremely large hospitals since machines cannot easily be shared. Transportation allows hospitals to share the capital cost, allowing for even small hospitals to provide IOERT services profitably.

Medicare has not reimbursed the IOERT market for many reasons, but from a practical point of view reimbursement would cause a misallocation of capital since the current class of IOERT machines are unable to be transported between hospitals efficiently. Although they claim to be transportable between hospitals, the machines must be calibrated for at least three energies of the machine to ensure proper function according to some studies. In the end, this amounts to three energies and multiple collimators to create different treatment fields. Prior to use of the machine on a patient one must test at least the energy being delivered for surgery and the ability to change the beam to one energy above and below the prescribed dose. This type of testing is called calibration. Calibration must be done every time the machine is moved between hospitals to ensure it is working in the way intended.

One can find boluses for use in radiation therapy at the following website: http://www.dotdecimal.com/products/ect. The following patent references are incorporated herein by reference: U.S. Pat. No. 8,094,779, U.S. Pat. No. 8,073,105, U.S. Pat. No. 5,037,374, U.S. Pat. No. 6,381,304, U.S. Pat. No. 7,834,336, U.S. Pat. No. 8,106,371.

BRIEF SUMMARY OF THE INVENTION

It is believed that Precision Accelerators's machines will be three times as fast as the prior art machines in terms of calibration. Every time a prior art machine that varies its energy powers up after transport, it must be tested at three different energies to show that the machine is working. Precision Accelerators's machine can only produce one energy and thus need only be calibrated to this single energy. All else being equal, removing energy variation in the head of the machine and moving it to the end of the collimator tube produces effectively the same treatment beam without having to calibrate the machine ad nauseum.

Inter-hospital transportation necessitates extremely quick calibration and quality assurance. The easiest beam to calibrate is a monoenergetic beam that is modified after the beam window because beam modification does not have to be included in linear accelerator quality assurance except as an attachment, which is tested at the same time the machine energy is. This saves a great deal of time because, instead of having to perform 5 tests for three different energies for a total of fifteen (15) tests, there are only five tests for one energy: 200 MU Test, 1000 MU/min test, and three tests of the 10 MeV beam with bolus output to verify beam.

The present invention includes two previous ideas put together in a unique way. The invention, although inspired by public ideas, is not obvious. Otherwise, the other manufacturers of machines on the market would simply have redesigned their machines with only one energy and modified the beam using a bolus to allow for transport. They never viewed their energy modification as a problem. Rather, they tout their technical prowess as a feature. The fact that one such competitor attempted to transport IOERT machines between hospitals, but after many attempts conceded that IOERT linear accelerators are not able to be effectively transported, demonstrates that they were unable to figure out a solution to both problems: beam stability and transportability. If the present invention were obvious, this competitor would have implemented it before now.

A third-generation of machines, see for example http://www.newrt.com/en/products/novac-11.html, uses collimators in order to create a homogeneous electron beam. These machines have a small, concentrated electron beam unsuitable for medical purposes coming out of the linear accelerator head that is transformed into a homogeneous, distributed beam as it runs through the length of the tube. This happens because of a repelling interaction between electrons within the tube, forcing the electrons to become evenly spread out while they travel through the tube. The Lucite brand poly (methyl methacrylate) tubing the collimator is made of absorbs aberrant electrons with minimal x-ray generation. After passing through a small amount of plastic film around the end of the tube before the breast that is meant to flatten the tissue, the electrons penetrate the potentially cancerous tissue on the surface of the breast, irradiating any remaining cancerous tissue.

A separate, but equally useful, invention is the tissue compensator aka a bolus to replace tissue (see, for example, the following website: http://vetmed.illinois.edu/4dvms/documents/imaging/RadTherapy/Overview.pdf). These are employed in radiation therapy to create a more homogeneous energy distribution in uneven tissue by compensating for any missing tissue. This is accomplished by inserting material that is of the same density as human tissue to compensate for the missing tissue. This technology can be employed for any type of radiation as the physics behind it are very simple: every 1 MeV of energy is an extra ½ cm to ⅓ cm of tissue penetration, depending on the exact density of the material chosen. The material chosen will be determined by empirical testing to decide which material gives the best results. The material is typically and preferably tissue isodense poly(methyl methacrylate). However, any hypo- or hyperdense material could be used in the same way, but one would need to take into account the difference in density between the human tissue and the material used.

While these two ideas have existed separately on the marketplace for many years, there has been no reason to put the ideas together because there was no application for isodense material before, after, or within a collimator tube for breast IOERT except as a means to increase the dosage to the skin. Even after three generations of machines, companies producing the prior art machines choose to use an electronic system of attenuating beam energy because they apparently believe this is the best way to vary energies in IOERT devices despite its higher cost and increased complexity. They did not choose modification of the electron beam through a compensator though it would produce results. Other manufacturers apparently simply do not see the advantage of this method over electronic variation.

An alternative method (an embodiment of the present invention) of attenuating the energy of an electron beam is to place isodense material (an isodense filter) in the path of the beam before it hits the tissue. By placing material in the way of the beam, there is the same effect of reducing the electron beam energy. Every 1 cm of isodense material reduces the depth the beam penetrates the tissue by about 1 cm. This is the same as reducing beam energy by about 3 MeV since the beam is penetrating the same amount of material of the same density. The actual radiation dose is determined by the output of the machine head as measured by dosimeters; however the depth of penetration is determined by the energy of the electron beam or, in the present invention, by the use of bolus not the energy (and thus speed) of the electrons in the beam. The only difference between an electrically-modulated beam with a bolus to remove the skin-sparing dose and a pure bolus system is calibration time. The treatment is otherwise identical. The compensator/bolus thickness for materials of densities other than that of human tissue will vary and are not standardized. By combining these interchangeable compensators/boluses of varying thicknesses with industrial electron linear accelerators, one can create a medical-grade, transportable linear accelerator. The bolus collimator is, in effect, creating transportable, stable, industrial-strength, robust linear accelerators for medical use out of industrial linear accelerators since what really makes an electron beam therapy device a medical device is the ability to vary the dose from patient-to-patient.

A very clear advantage of using a bolus as opposed to electronic variation is that the air/tissue interface is effectively moved away from the tissue being treated and is instead present at the air/isodense material interface. In this manner the skin-sparing dose is moved away from the tissue being treated. This allows all of the tissue being treated to receive 100% of the prescribed radiation dose. In the case of external beam compensation, the skin-sparing dose is desirable because there is skin which is highly sensitive to radiation between the beam and the cancerous tissue. Since the skin is treated in external electron beam, it is desirable to minimize the dose the skin receives. However, since IOERT is performed when the skin is not in the way of the beam, there is no need for this skin-sparing dose. Accordingly, there is no negative effect, and arguably a positive effect, associated with having a large compensator in front of an electron beam used in breast IOERT treatment.

An advantage of the present compensator based mechanism for changing the depth of penetration of the operative electron beam method is the calibration efficiencies. Originally, calibration efficiencies were not a concern because the stationary machines were in a dedicated, shielded room and did not need to be calibrated daily. Upon invention of intra-hospital mobile devices, the patient-treatment volume did not require the current manufacturers to solve the problem of radiation safety limits from frequent, radiation-intensive calibration, which lowers the maximum number of patients. The best solution to the problem of the inversely correlated nature between patient number and radiation exposure is to minimize unnecessary radiation exposure. In other words, the only way to increase patients is to reduce calibration time, thereby reducing the radiation used in the process. Since patient treatment and machine calibration are both components of the allowable total machine usage in a given day, one can increase the patient volume by decreasing the time required for calibration of the machine Suitable materials for this isodense filter include isodense materials made up primarily or entirely of carbon, oxygen, and hydrogen, such as: poly(methyl methacrylate) (PMMA—a transparent thermoplastic sold under the trademarks Lucite, Plexiglas, and Perspex, for example), Delrin brand acetal resin, UHMW (ultra-high molecular weight polyethylene), polyethylene, polypropylene, ABS, acrylic, Bakelite, CPVC, fiberglass, Kynar brand plastic, Lexan brand plastic, Micarta brand plastic, PVC, Ryton brand plastic, and Teflon brand polytetrafuoroethylene, when the tissue is human breast tissue. Tissue compensators used for electron beam preferably require low atomic number materials so as to minimize the amount of Brehmstrahlung x-rays that are created.

While preferably the density of the isodense filter is the same as the tissue which is being radiated, the density could vary, though preferably not more than 2% so as to not dramatically change the tissues treated.

While virtually any material can be used as a collimator filter in the present invention, it is preferable that the density is the same as human tissue or roughly that. This makes it easier in two ways. First, if a patient has a breast that needs to be treated to a depth less than the 3.3 centimeters (the 10 Mev electron beam by definition has a 90% isodose line of penetration located at 3.3 cm), a corresponding filter could be used to reduce the amount of penetration by the level that would be required to move the tissue penetration less deeply in the tissue. For example if an oncologist wishes the 90% isodose line to be at 2.3 centimeters in the breast rather than 3.3 cm he can prescribe a 1 cm tissue isodense bolus to bring the 90% isodose line to 2.3 centimeters. There is minimal math needed. Second, there are many isodense materials available for manufacturing, such as poly(methyl methacrylate), which is desirable because it is inexpensive plastic. One can make many boluses cheaply from this material.

The bolus is preferably a solid shape which may be attached to a collimator of preferably isodense material. The bolus is preferably a solid cylinder of isodense material, such as plastic, and preferably Lucite. It is preferably attached to a hollow cylinder of Lucite (the collimator tube). Preferably, the bolus and hollow cylinder are integral. Calibration for the 10 meV beam would preferably be done at 100 cm source surface distance. The additional bolus would in the preferred embodiment be added to create a dosimetrically equivalent beam when less penetration is desired. This makes variation of depth penetrance simple and intuitive for the radiation oncologist. To move the 90% isodose line 1 cm less in tissue, one can advantageously use a 1 cm tissue isodense material duplicating the dosimetric characteristics of a 7 MeV electron beam. To duplicate a 6 MeV electron beam one could use a 1.3 cm attenuator. This actually allows for more precise dosimetry than is currently available since the depth of the 90% isodose curve may be moved in smaller increments.

Other machines have a computer and electronics which are subject to malfunction, varying the energy of the beam. Precision Accelerators is the only company to only change the characteristics of the beam after it has come out of the head of the IOERT machine. This makes the Precision Accelerators machine extremely stable.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings (which, for ease of illustration, are not to scale), wherein like reference numerals denote like elements and wherein.

DETAILED DESCRIPTION OF THE INVENTION

In order to provide for a multiple energy linear accelerator using a single energy machine, multiple collimators can be created with boluses 21-27 of many different thicknesses to provide doctors with the most treatment flexibility. Ideally, there will be a series of seven removable collimator tubes 15 with boluses 21-27 (preferably integral with tube 15, but boluses 21-27 could instead be suitably attached in some fashion which would not allow leaking of the beam around the boluses 21-27), along with a tube 15 without a bolus in the event that the full energy of the monoenergy beam is desired for treatment. With seven boluses of 0.333 cm increasing increments, the beam energy (and thus speed of electrons) can be changed from 10 MeV (no bolus) to 9 MeV (0.333 cm material) all the way to 3 MeV (2.333 cm material). Below a beam energy of 3 MeV, the beam does not penetrate even 1 cm of breast tissue, too low energy to be therapeutic in most cases. The bolus 21-27 is preferably a solid cylinder of isodense material, such as plastic, and preferably Lucite. It is preferably attached to a hollow cylinder of Lucite (the collimator tube 15). Preferably, the bolus 21-27 and hollow cylinder 15 are integral.

While perhaps the bolus could be placed at any area in the length of the tube, it is preferred to place the bolus 21-27 at the end of the tube 15 closest to the breast, which will provide the patient with the most homogeneous electron beam for treatment as the beam has run the entire length of the typically 100 cm hollow tube 15 before reaching bolus 21-27. In addition the flattening and the symmetry of the beam is at the end of the collimator since there would be some Brehmstrahlung x-rays generated by interaction with the bolus and the calibration would be greatly complicated.

Figure 1:
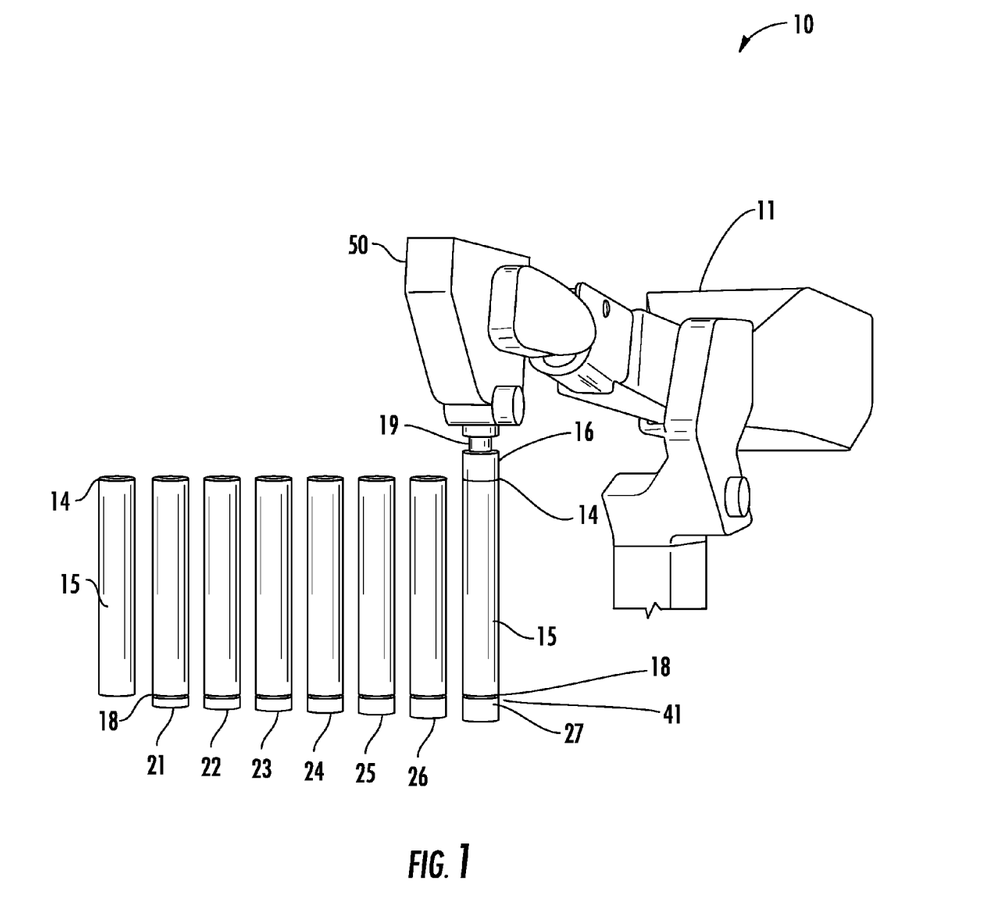
FIG. 1 is a perspective view of a preferred embodiment of the apparatus of the present invention.

FIG. 1 is a perspective view showing a preferred embodiment of the present invention, IOERT apparatus 10. Apparatus 10 includes an IOERT machine 11, which could be a simple, relatively non-expensive mono-energy industrial linear accelerator which produces 10 MeV of radiation. Machine 11 is preferably an industrial, durable, accelerator with technology stable enough for transport from hospital to hospital. A collimator tube 15, preferably made of PMMA (sold as Lucite, for example), is attached to the head 50 of machine 11 using a plastic tube 16 and a connector 19. A plurality of boluses 21, 22, 23, 24, 25, 26, 27, increasing in size from 1/3 cm to 2 1/3 cm in 1/3 cm increments, is preferably included (though other sizes could be used to make the increments greater or smaller). These filters 21-27 are preferably made of isodense materials made up primarily or entirely of carbon, oxygen, and hydrogen, such as poly(methyl methacrylate) (PMMA), Deirin brand acetal resin, UHMW (ultra-high molecular weight polyethylene), polyethylene, polypropylene, ABS (Acrylonitrile butadiene styrene), acrylic, Bakelite, CPVC (Chlorinated polyvinyl chloride), fiberglass, Kynar brand plastic, Lexan brand plastic, Micarta brand plastic, PVC (polyvinyl chloride), Ryton brand plastic, and Teflon brand polytetrafluoroethylene, when breast tissue is being treated. Preferably, the boluses 21-27 are integral with tube 15, and the distance from the top 14 of tube 15 to the top of the boluses 21-27 (as shown in FIG. 1) is the same for each tube 15 and bolus (100 cm, for example). Thus, for example, the total length of tube 15 and bolus 21 would be 100 1/3 cm, and the total length of tube 15 and bolus 27 would be 102 1/3 cm.

Figure 2:
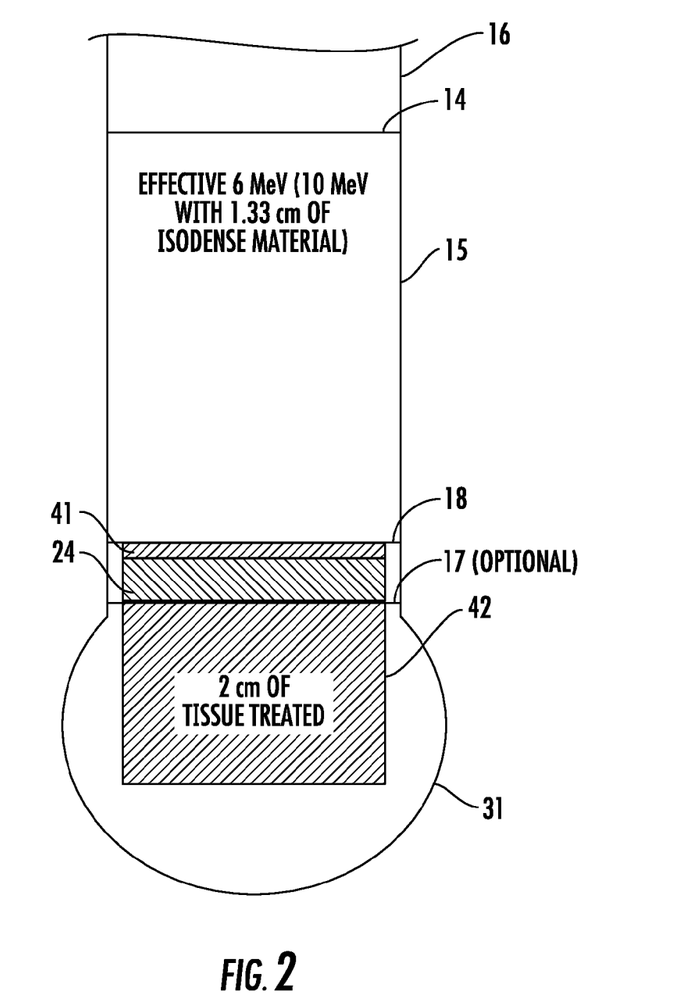
FIG. 2 is a detail of a preferred embodiment of the apparatus of the present invention (not to scale)

FIG. 2 shows a detail of the present invention in use when treating the breast 31 of a human patient, with optional cling wrap 17 over the distal end of collimator tube 15 and a bolus 24 which is preferably integral with tube 15 and is present at the distal end of collimator tube 15 to reduce the radiation entering the breast 31 from 10 MeV to 6 MeV.

Figure 3:
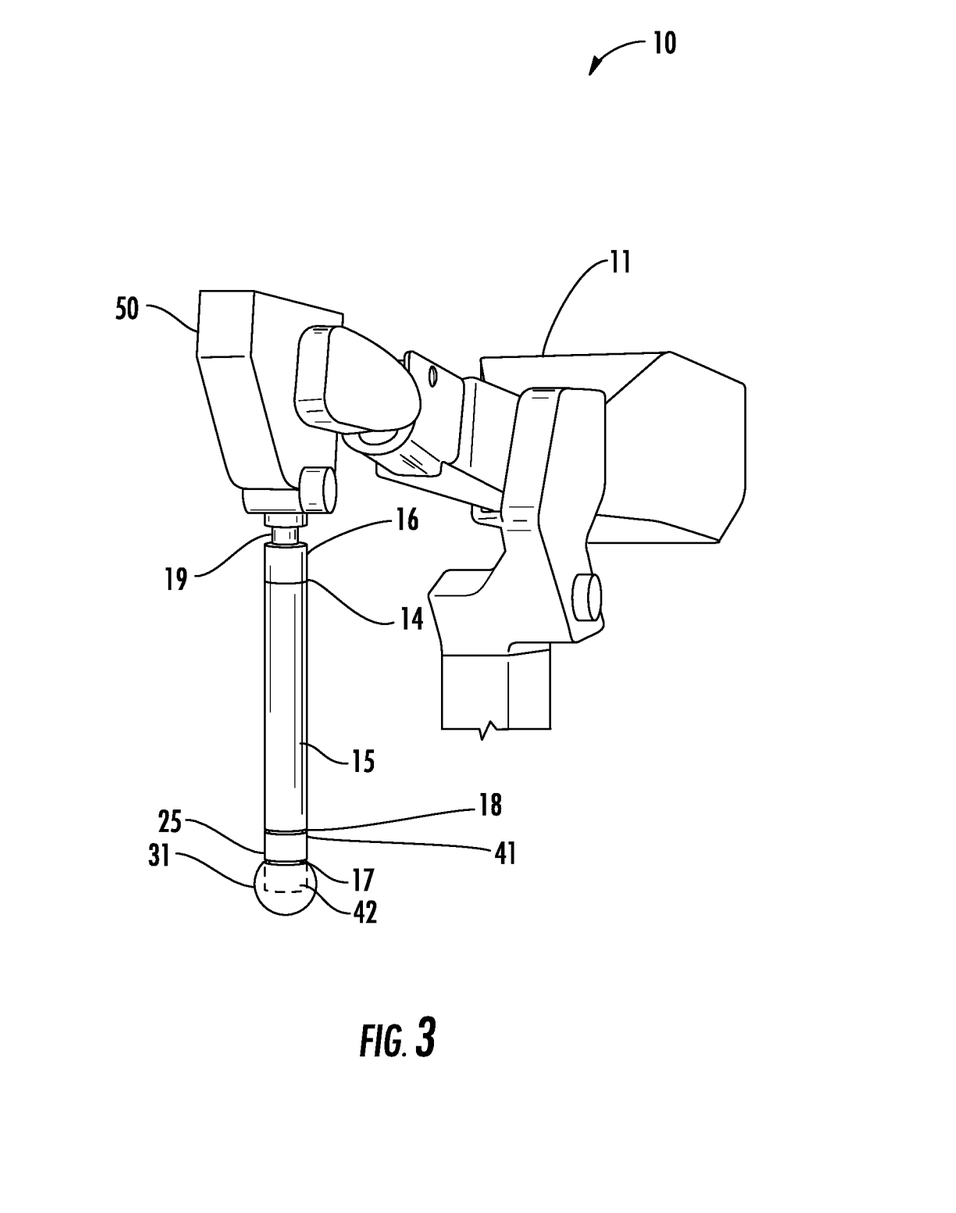
FIG. 3 is a top view of a preferred embodiment of the apparatus of the present invention in use.
Figure 4:
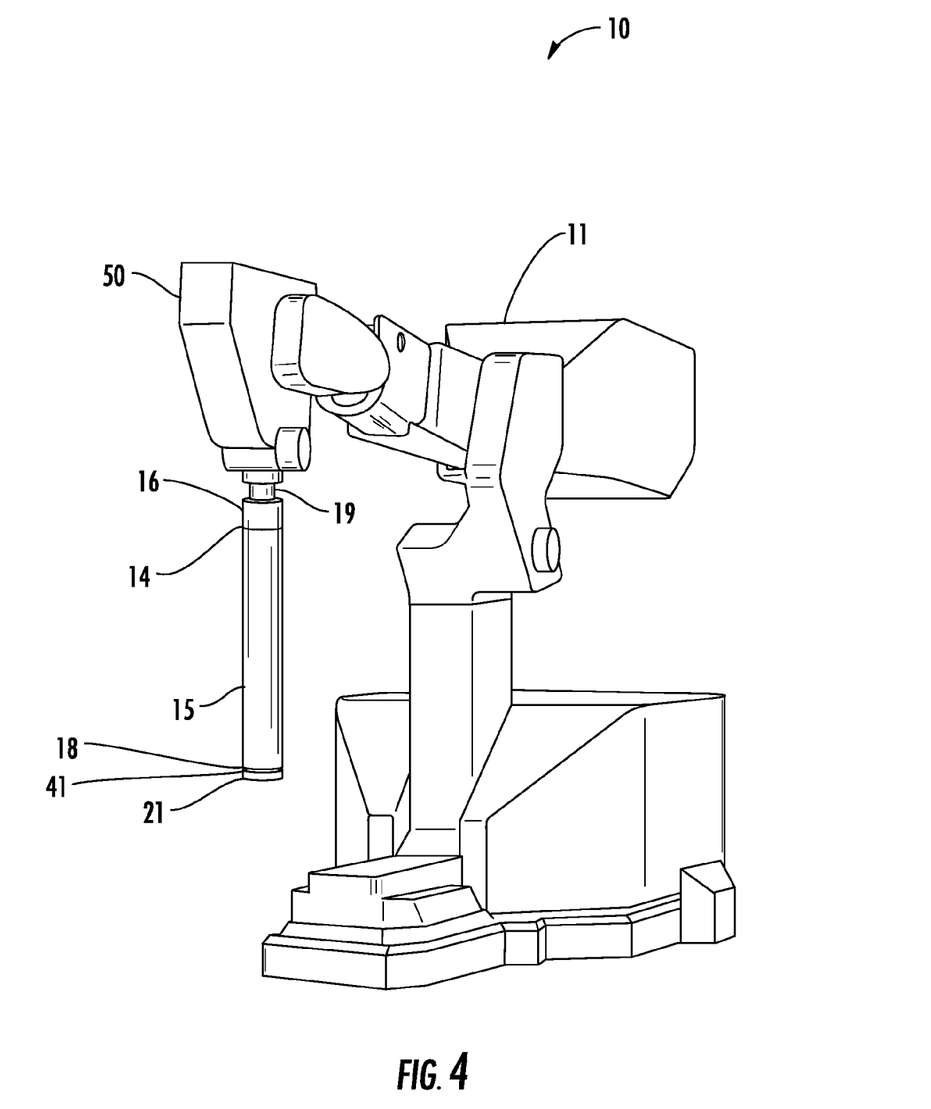
FIG. 4 is a perspective view of a preferred embodiment of the apparatus of the present invention showing it ready to be used with a supine patient.

In FIG. 3, apparatus 10 is shown in use to treat a breast 31 of a patient. A bolus 25 is shown integrally attached to tube 15. Optional cling wrap 17 is shown over the distal end of bolus 25. Bolus 25 will reduce the radiation reaching breast 31 from 10 MeV to 5 MeV (as 5 MeV of energy will be dissipated as the electrons flow through bolus 25). Treatment area 42 extends 1 2/3 cm into breast 31 in this example, as bolus 25 is 1 2/3 cm thick (as shown in FIG. 5, 10 MeV would normally extend 3 1/3 cm into the breast 31—the 1 2/3 cm thick bolus 25 pulls 1 2/3 cm of that energy region upward into bolus 25, leaving just 1 2/3 of breast 31 to be treated).

Figure 7:
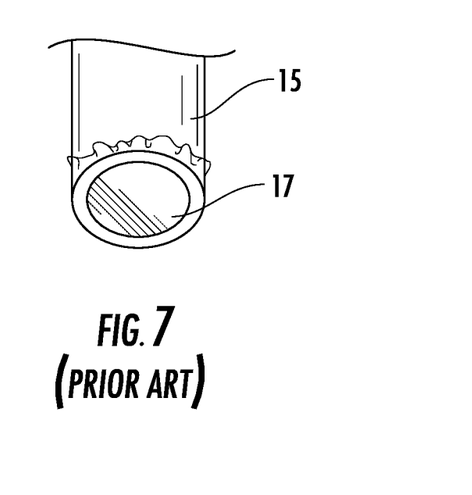
FIG. 7 is a detail of a prior art system.

FIG. 7 shows a detail showing disposable plastic cling wrap 17 (which could be for example Glad brand cling wrap or plastic wrap by Saran) stretched over the end of tube 15 proximal the breast 31 (not shown) to flatten breast and/or minimize the chance of direct bolus contact with body fluids 31 and allow even penetration of the radiation from an IOERT machine. Cling wrap 17 could be used as well with the present invention, though when boluses 21-27 are integral with tube 15, the boluses would flatten breast 31 and allow even penetration of the radiation from an IOERT machine, even without cling wrap 17.

Figure 5:
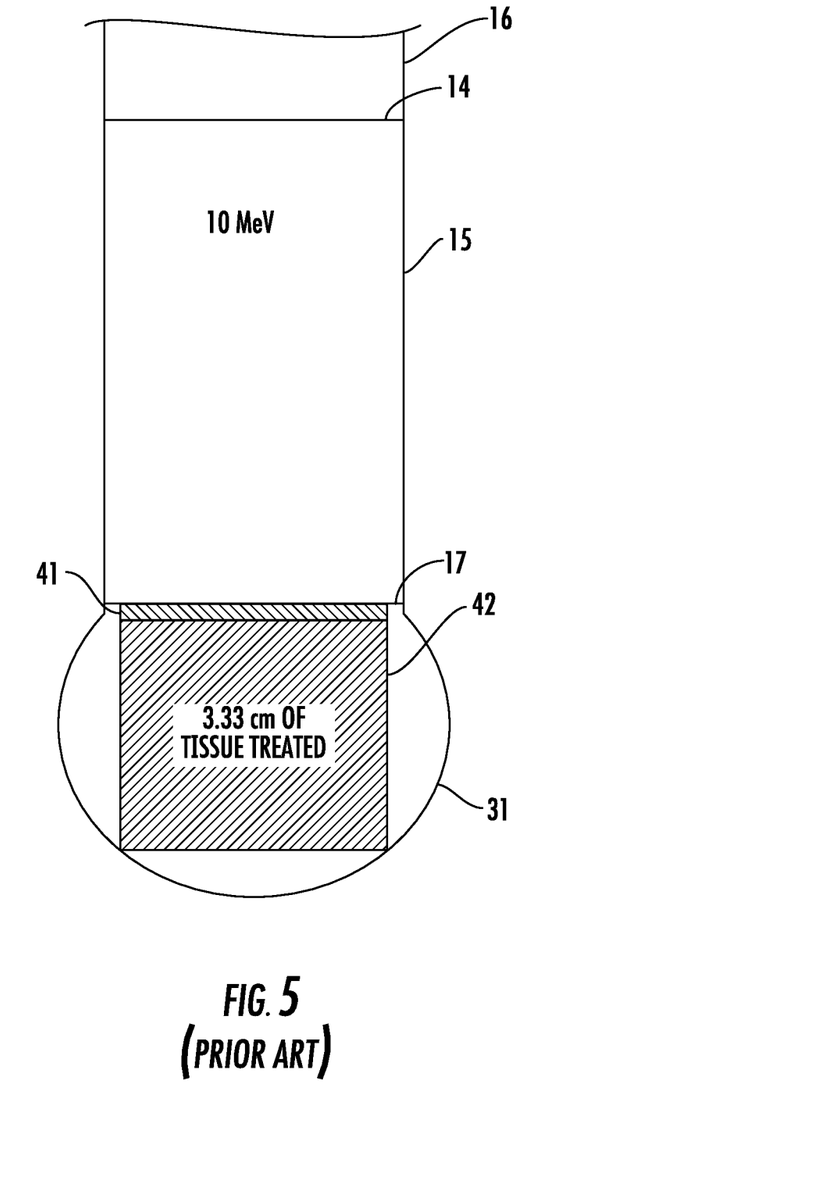
FIG. 5 is shows a prior art IOERT system (not to scale)
Figure 6:
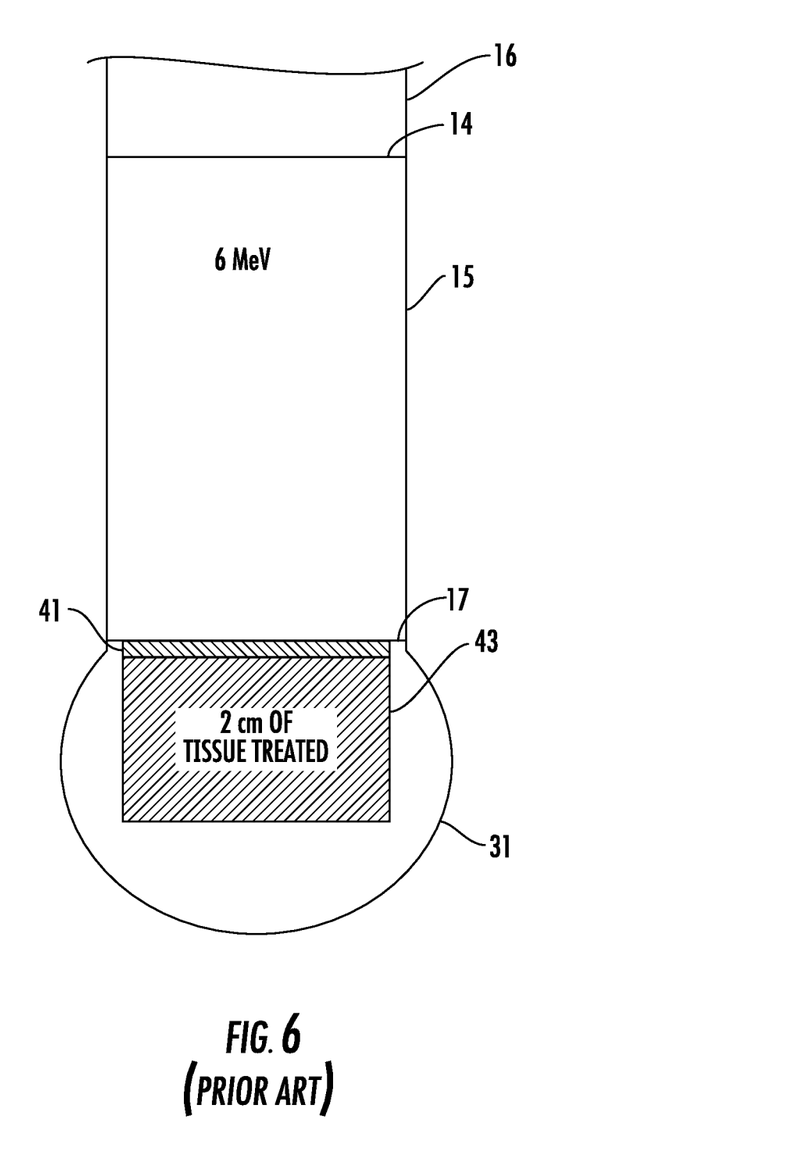
FIG. 6 shows a prior art IOERT system (not to scale)

FIGS. 5 and 6 show prior art IOERT systems in which the amount of radiation reaching the breast 31 is controlled electronically, rather than with the use of boluses 21-27 of the present invention. As can be seen in FIG. 5, a 10 MeV beam will typically penetrate and treat 3⅓ cm of breast 31 tissue, while a 6 MeV beam (see FIG. 6) will typically penetrate and treat 2 cm of breast 31 tissue.

While theoretically one can use just about any type of material for boluses 21-27, it is best to use an isodense material (a material which has roughly the same density as human breast tissue) because it avoid some problems of other densities. With an isodense material such as poly(methyl methacrylate), little math is needed to determine how much to use; one simply determines the amount of attenuation desired and selects the collimator tube 15 with the bolus 21-27 that corresponds to that attenuation (bolus 21 for 1 MeV, bolus 22 for 2 MeV, etc.).

If one uses a material with a high atomic number like lead, more of the radiation will be transformed into Bremsstrahlung, through the interaction of the treatment beam electrons with the nucleus of the molecules they pass by in the bolus. Brehmstrahlung is produced when the electron beam hits the tissue, but this happens regardless of the method of energy attenuation. Bremsstrahlung is just a statement of the conservation of energy in an indirect manner. When the electrons have their energy and/or direction changed, some of this energy is released in the form of other radiation, like heat or x-rays. This is Bremsstrahlung. One wants to minimize this during radiation treatment since Bremsstrahlung is a more penetrating form of radiation and has much greater shielding requirements If one uses too dense a material, there are two problems: 1) the precision of the width of the bolus increases dramatically (if one used an extremely dense material, the difference between boluses would be measured in mm, not cm) and 2) more Bremsstrahlung radiation is created. Imagine electrons going into a tight net. The larger the atomic number and thus atoms, the smaller the holes. With smaller holes, more electrons hit the net, causing the string to vibrate. In this example, the vibrations would be Bremsstrahlung.

Using a material that is less dense than tissue theoretically could be advantageous as there is less decelerating radiation because there are lower atomic number atoms involved and thus smaller nuclei. Ideally, if Bremsstrahlung were the only concern, one would want to use hydrogen gas compressed to a density near that of tissue as this would produce the least Bremsstrahlung since hydrogen is the smallest nucleus in the universe known to man. Unfortunately, hydrogen gas is highly explosive and not suitable for this purpose. While using other gases would work as well, this method is cost prohibitive because the manufacturing process would be much more complicated than injecting Lucite into a mold. In addition to higher manufacturing costs, the compressed-gas bolus would be extremely prone to breaking if dropped as it is hollow with a highly compressed gas inside, unlike Lucite which is a solid block of plastic. Moreover, most doctors use isodense material and it is the standard, therefore no real research has been done into a hypodense bolus.

The collimator filters or boluses 21-27 can be held in place on the distal end of tube 15 with a simple t-bone clamp (such as that shown in http://www.hclfasteners.com/shoppdfs/t-bolt.pdf). This method helps to ensure that there a tight fit that is perfectly aligned with the end of the collimator tube 15. It is preferable for the collimator filters 21-27 to have a diameter substantially equal to the outer diameter of tube 15 so that all or substantially all radiation traveling through tube 15 likewise travels through a filter 21-27 (otherwise, there could be areas where the radiation would go deeper into the patient's tissue than desired). The present inventor believes that the best way to achieve this is to simply make the collimator filters 21-27 integral with collimator tube 15. Other possible, but not preferred, means of attachment of boluses 21-27 to tubes 15 include a screw-on bolus, tape to hold the bolus on, a t-bolt clamp, or even the right size thick rubber band. The problem with all of these methods is that they introduce human error, which can be just as dangerous as computer error. Therefore, the preferred means of attachment that maintains the safety of removing a computer, while not introducing any other errors, is making the bolus part of the collimator.

The diameter of collimator tube 15 and collimator filters 21-27 can be, for example, about 1-30 cm, preferably about 2-25 cm, more preferably about 3-15 cm, and for example about 5 cm or 10 cm. The length of collimator tube 15 can be, for example, about 95.5-104.5 cm, preferably about 98-102 cm, more preferably about 99-101 cm, and for example about 100 cm.

Precision Accelerators will have a machine that is more stable and more precise because it uses a physical method of modulation. As long as its PMMA boluses 21-27 are accurate enough, the apparatus 10 will modulate the beam better, without need for extensive electronics, than the current methods do allowing for transportation. The present inventor believes that all competitors of Precision Accelerators use a method of varying their energy that is directly proportional to beam error bands. This is because electronically varying the current cannot go below a certain unit of accurate variation. This is what every system uses. Precision Accelerators's physical method is a more precise method of varying the exact electron energy and direction because it is physically verified and therefore has no error. The beam variation is reduced to insignificant levels for virtually no additional cost, while increasing the features of the machine to daily inter-hospital transport. While the difference is subtle, the means of variation has a large impact on the way Precision Accelerators's machine is used, increasing efficiency.

The present inventor believes that the best way to join a bolus 21-27 to the tube 15, which must be confirmed by testing, is to make the bolus 21-27 integral with the collimator tube 15 when molding the tube 15. This allows the system to use existing interlocks and not have to engineer anything else. Moreover, it is very difficult to lose or break a 100+ cm tube of thick plastic. Therefore, it is highly unlikely that this will be lost. As long as this is not inefficient in setting up, this is most likely the best because there will be no parts lost.

PARTS LIST

The following is a list of parts and materials suitable for use in the present invention:
Parts Number Description
10 IOERT apparatus of the preferred embodiment of the present invention
11 IOERT machine (such as an industrial linear accelerator, such as a 10 MeV Portac model produced by L&W Research Inc. of Connecticut—http://www.lwresearch.com/products/portae/portac.html)
14 connector between tube 15 and tube 16
15 plastic collimator tube (such as PMMA)
16 plastic tube connecting collimator tube 15 to IOERT machine 11

17 plastic cling wrap placed over proximal (to patient) end of tube 15 to flatten breast 31
18 connection when boluses 21-27 are not integral with tube 15—otherwise, boundary between open tube 15 and boluses 21-27 when tube 15 and boluses are integral
19 connector between tube 16 and IOERT machine 11
21 ⅓ cm thick bolus (such as PMMA)
22 ⅔ cm thick bolus (such as PMMA)
23 1 cm thick bolus (such as PMMA)
24 1⅓ cm thick bolus (such as PMMA)
25 1⅔ cm thick bolus (such as PMMA)
26 2 cm thick bolus (such as PMMA)
27 2⅓ cm thick bolus (such as PMMA)
31 human breast being treated for cancer
41 region of skin-sparing dose
42 region of 100% energy at 10 MeV
43 region of 100% energy at 6 MeV
50 energy producing head of IOERT machine 11

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A method of controlling the amount of energy to reach a breast cancer patient undergoing intraoperative electron radiation therapy, comprising:
   providing an intraoperative electron radiation therapy machine having a head for producing a monoenergetic beam;
   selecting a bolus made of a material having substantially the same density as human breast tissue and placing the bolus between the head of the machine and the patient to change the energy of a monoenergetic beam after the monoenergetic beam has left the part of the machine that accelerates the electrons to the desired energy, the bolus being chosen to reduce the energy traveling through the tube to a desired amount of energy to treat the patient.

2. The method of claim 1, wherein the bolus is integral with a collimator tube which attaches to the head of the intraoperative electron radiation therapy machine.

3. The method of claim 2, wherein the tube is made of poly(methyl methacrylate).

4. The method of claim 1, wherein the bolus comprises at least one material from the group consisting of isodense materials made up primarily or entirely of carbon, oxygen, and hydrogen, such as PMMA, Delrin brand acetal resin, UHMW (ultra-high molecular weight polyethylene), polyethylene, polypropylene, ABS, acrylic, Bakelite, CPVC, fiberglass, Kynar brand plastic, Lexan brand plastic, Micarta brand plastic, PVC, Ryton brand plastic, and Teflon brand polytetrafluoroethylene.

5. The method of claim 1, wherein the bolus comprises poly(methyl methacrylate).

6. The method of claim 1, further comprising calibrating the intraoperative electron radiation therapy machine after it is moved and before it is used to treat a patient.

7. A method of controlling the amount of energy to reach a breast cancer patient undergoing intraoperative electron radiation therapy, comprising:
   providing an intraoperative electron radiation therapy machine having a head for producing a beam;
   controlling the intraoperative electron radiation therapy machine such that the head produces a monoenergetic beam during calibration of the machine and treatment of the patient;
   calibrating the intraoperative electron radiation therapy machine after it is moved and before it is used to treat a patient;
   selecting a bolus made of a material having substantially the same density as human breast tissue and placing the bolus between the head of the machine and the patient to change the energy of a monoenergetic beam after it has left the machine, the bolus being chosen to reduce the energy traveling through the tube to a desired amount of energy to treat the patient.

8. The method of claim 7, wherein the bolus is integral with a collimator tube which attaches to the head of the intraoperative electron radiation therapy machine.

9. The method of claim 8, wherein the tube is made of poly(methyl methacrylate).

10. The method of claim 7, wherein the bolus comprises at least one material from the group consisting of isodense materials made up primarily or entirely of carbon, oxygen, and hydrogen, such as poly(methyl methacrylate), Delrin brand acetal resin, UHMW (ultra-high molecular weight polyethylene), polyethylene, polypropylene, ABS, acrylic, Bakelite, CPVC, fiberglass, Kynar brand plastic, Lexan brand plastic, Micarta brand plastic, PVC, Ryton brand plastic, and Teflon brand polytetrafluoroethylene.

11. The method of claim 7, wherein the bolus comprises poly(methyl methacrylate).

12. Apparatus for performing electron radiation therapy on a patient, the apparatus comprising:
   a plurality of boluses for use with an intraoperative electron radiation therapy machine having a head for producing an energy beam, the boluses made of a material having substantially the same density as human tissue for placement between the head of the machine and the patient to change the energy of a beam after it has left the machine, the bolus being chosen to reduce the energy traveling through the tube to a desired amount of energy to treat the patient.

13. The apparatus of claim 12, wherein the boluses comprise at least one material from the group consisting of isodense materials made up primarily or entirely of carbon, oxygen, and hydrogen, such as poly(methyl methacrylate), Delrin brand acetal resin, UHMW (ultra-high molecular weight polyethylene), polyethylene, polypropylene, ABS, acrylic, Bakelite, CPVC, fiberglass, Kynar brand plastic, Lexan brand plastic, Micarta brand plastic, PVC, Ryton brand plastic, and Teflon brand polytetrafluoroethylene.

14. The apparatus of claim 12, wherein the boluses comprise poly(methyl methacrylate).

15. The apparatus of claim 12, further comprising a collimator tube.

16. The apparatus of claim 15, wherein the tube is made of at least one material from the group consisting of isodense materials made up primarily or entirely of carbon, oxygen, and hydrogen, such as poly(methyl methacrylate), Delrin brand acetal resin, UHMW (ultra-high molecular weight polyethylene), polyethylene, polypropylene, ABS, acrylic, Bakelite, CPVC, fiberglass, Kynar brand plastic, Lexan brand plastic, Micarta brand plastic, PVC, Ryton brand plastic, and Teflon brand polytetrafluoroethylene.

17. The apparatus of claim 15, wherein the tube is made of poly(methyl methacrylate).

18. The apparatus of claim 12, wherein at least some of the boluses are integral with collimator tubes.

19. The apparatus of claim 12, further comprising the intraoperative electron radiation therapy machine.

20. Apparatus for performing electron radiation therapy on a breast cancer patient, the apparatus comprising:
- an intraoperative electron radiation therapy machine having a head for producing a beam of energy;
- an intraoperative electron radiation therapy collimator tube connected to the intraoperative electron radiation therapy machine;
- a plurality of boluses made of a material having substantially the same density as human breast tissue to change the energy of a beam after the beam has left the head of the machine, allowing a bolus to be chosen to reduce the energy traveling from the head to a desired amount of energy to treat the patient.

21. The apparatus of claim 20, wherein the boluses comprise at least one material from the group consisting of isodense materials made up primarily or entirely of carbon, oxygen, and hydrogen, such as poly(methyl methacrylate), Delrin brand acetal resin, UHMW (ultra-high molecular weight polyethylene), polyethylene, polypropylene, ABS, acrylic, Bakelite, CPVC, fiberglass, Kynar brand plastic, Lexan brand plastic, Micarta brand plastic, PVC, Ryton brand plastic, and Teflon brand polytetrafluoroethylene.

22. The apparatus of claim 20, wherein the boluses comprise poly(methyl methacrylate).

23. The apparatus of claim 20, wherein the tube is made of at least one material from the group consisting of isodense materials made up primarily or entirely of carbon, oxygen, and hydrogen, such as poly(methyl methacrylate), Delrin brand acetal resin, UHMW (ultra-high molecular weight polyethylene), polyethylene, polypropylene, ABS, acrylic, Bakelite, CPVC, fiberglass, Kynar brand plastic, Lexan brand plastic, Micarta brand plastic, PVC, Ryton brand plastic, and Teflon brand polytetrafluoroethylene.

24. The apparatus of claim 20, wherein the tube is made of poly(methyl methacrylate).

25. The apparatus of claim 20, wherein at least some of the boluses are integral with collimator tubes.

26. The apparatus of claim 20, wherein the head produces a beam of a single energy.

27. The method of claim 7, wherein the intraoperative electron radiation therapy machine produces a beam of a single energy.

28. The method of claim 7, wherein the intraoperative electron radiation therapy machine produces a beam of about 10 MeV.

* * * * *